(12) United States Patent
Qi et al.

(10) Patent No.: US 7,971,848 B2
(45) Date of Patent: Jul. 5, 2011

(54) IN-SITU GEL CASTING MACHINE

(76) Inventors: Xiaoqiang Qi, Gansu (CN); Xiudong Gao, Beijing (CN); Shidong Wang, Beijing (CN); Cunlu Dong, Beijing (CN)

( * ) Notice: Subject to any disclaimer, the term of this patent is extended or adjusted under 35 U.S.C. 154(b) by 348 days.

(21) Appl. No.: 12/439,541

(22) PCT Filed: Jun. 22, 2007

(86) PCT No.: PCT/CN2007/070164
§ 371 (c)(1),
(2), (4) Date: Mar. 1, 2009

(87) PCT Pub. No.: WO2008/025264
PCT Pub. Date: Mar. 6, 2008

(65) Prior Publication Data
US 2010/0200406 A1    Aug. 12, 2010

(30) Foreign Application Priority Data

Sep. 1, 2006 (CN) ...................... 2006 2 0138476 U

(51) Int. Cl.
*B29C 41/16* (2006.01)
*C25B 9/00* (2006.01)

(52) U.S. Cl. ........ 249/129; 249/139; 249/161; 204/470; 204/616; 204/618; 204/619

(58) Field of Classification Search .................. 249/112, 249/120, 139, 155, 158, 161; 204/470, 616, 204/618, 619, 620; 425/318
See application file for complete search history.

(56) References Cited

U.S. PATENT DOCUMENTS

| 4,574,040 | A | * | 3/1986 | Delony et al. | 204/606 |
| 5,013,420 | A | * | 5/1991 | Schuette | 204/614 |
| 5,626,735 | A | * | 5/1997 | Chu | 204/606 |
| 6,942,775 | B1 | * | 9/2005 | Fox | 204/470 |
| 7,276,143 | B2 | * | 10/2007 | Chen | 204/618 |
| 7,867,372 | B2 | * | 1/2011 | Cheung et al. | 204/618 |

* cited by examiner

*Primary Examiner* — Robert B Davis
*Assistant Examiner* — Thu Khanh T Nguyen
(74) *Attorney, Agent, or Firm* — Global IP Services; Tianhua Gu

(57) ABSTRACT

An In-Situ gel casting machine comprising a gel casting stand (1), a rubber cushion (2), and a locking base (3). Overlapping a notched glass (121) with a glass plate (122) tightly together will form a gel room (123), it is called as the slab gel casting mold (12). Put the same two slab gel casting molds (12) into each side of the portable casting stand (11) along its insides, and then insert the wedge frames (13) against each slab gel casting mold (12), which will form the gel-casting stand (1). Because each sidewall locking structure (32) of the locking base (3) compresses the slab gel casting molds from two directions, it ensures that the slab gel casting molds are sealed well. Without moving the slab gel casting molds, an electrophoresis experiment can be started right after the gel has been solidified, which can avoid the leakage of the gel solution and the production of air bubbles into the slab gel casting molds.

9 Claims, 3 Drawing Sheets

IN-SITU GEL CASTING MACHINE

FIELD OF THE INVENTION

The invention relates, in general, to an experimental instrument, and more particularly, to a perfusion equipment for gel casting for electrophoresis experiments.

BACKGROUND OF THE INVENTION

The common way of casting gel is to use the silicone cushion gland strip method in the most electrophoresis experiments. A gel room normally contains a notched glass plate, a glass plate, a u-shaped silicone cushion gland strip, and four clips. Put the gel room vertically with tools and then pour the gel into the system. Because the gel has to be solidified before doing the analysis, it will reduce the efficiency of the experiment, complicate the procedure of casting gel, and lower the gel quality. After completing the gel casting, the U-shaped silicone cushion gland also must be removed before running the experiment. This can cause the leakage of gel from the gel room, produce some air bubble into the gel room and increase the difficulty of making the bottom side of gel evenly. In general, the common way of casting gel complicates its operation and makes experimental results usually unstable.

SUMMARY OF THE INVENTION

In respect to the aforementioned background, it is one purpose of the invention to develop an in-situ gel casting machine having improved slab gel casting molds and with a locking base added in order to compress the slab gel casting molds tightly from two directions to avoid air bubbles and leakage of gel and consequently ensuring the experiment being started without moving the slab gel casting molds.

The present invention is directed towards an "In-Situ Gel Casting machine". An in-situ gel casting machine comprising: a gel-casting stand device including a portable casting stand with a pair of wedge groove, a slab gel casting mold and a wedge frame both being inserted into the wedge groove and both being clamped together by a clamping force brought from the wedge groove; a base having four locking blocks to defined a area in which the gel-casting stand device is located movably; a sidewall locking device for pushing the wedge frame into the wedge groove further for getting a strong clamping force from the wedge groove; a rubber cushion being set on the base within the four locking blocks, the gel-casting stand device seating on the rubber cushion.

The In-Situ Gel Casting machine consisting of a gel-casting stand (1), a silicone cushion (2), and a locking base (3). The gel-casting stand (1) consists of a portable casting stand (11), two slab gel casting molds (12) and two wedge frames (13). Each of the slab gel casting molds (12) mainly contains a notched glass (121) and a glass plate (122) with spacer. Overlapping the notched glass (121) with the glass plate (122) tightly together forms a gel casting mold (123). The gel-casting stand (1) is formed by putting the same two slab gel casting molds (12) into each side of the portable casting stand (11) along its insides, and then insert the wedge frames (13) against each slab gel casting mold (12).

The locking base (3) consists of a base (31) with four locking blocks (311) and two sidewall-locking structures (32). Each of the two sidewall-locking structures (32) contains an eccenter axis body (35), a drive pin (34), and a pressing plate (36). The eccenter axis body (35) along its axis consists of eccenters (351), a U-slot stop (352), a pin roll locating hole (353), an O-slot (354) and a handle (33). Each lower part of the sidewall locking structure (32) has the drive pin (34) matching with the U-slot stop (352) and the O-slot (354). Each drive pin (34) consists of a bolt (343), a spring (342) and a pin (341) that can be elastically extended and compressed in the vertical direction. On each of the sidewall-locking structures (32), the press plate (36) is provided that face to the inside of the locking base (3). The press plate (36) hitches on the eccenter (351) and connects with a horizontal leading pole (37) that supports the press plate (36).

The overall structure of the "In-Situ Gel Casting machine" is as follows: the silicone cushion (2) is set on the base (31) of the locking base (3), and the gel-casting stand (1) is put onto the locking base (3) within the four locking blocks (311). Then, the handles (33) are pushed inwardly while the pins (341) of the drive pins (34) are in the U-slot stops (352) and the press plates (36) are moved to a proper distance to the slab gel casting molds (12). After this, the handles (33) are turn clockwise and the press plates (36) are set onto the lower beams of the wedge frames (13), which get the pins (341) of the drive pins (34) in the pin roll locating holes (353). Therefore, the press plates (36) will push the wedge frames that automatically compress the slab gel casting molds (12) tightly from two directions.

The invention is advantageous in following aspects:
1. Because of improving the structure of the slab gel casting mold (12) and assembling of the locking base (3), the "In-Situ Gel Casting machine" can obtain a new function that electrophoresis experiments can be started right after the gel has been solidified without moving the slab gel casting molds, which avoid the leakage of the gel solution and the production of air bubbles into the slab gel casting molds. In addition, the bottom edges of the gel can line up evenly with the edges of the slab gel casting molds (12). In general, this machine has improved the quality and the efficiency for electrophoresis experiments. It is also small, portable and can be easily handled.
2. This system is simple and compact for its structure, convenient and reliable to use, and easy to maintain and repair.

DETAILED DESCRIPTION THE INVENTION

Figure 1:
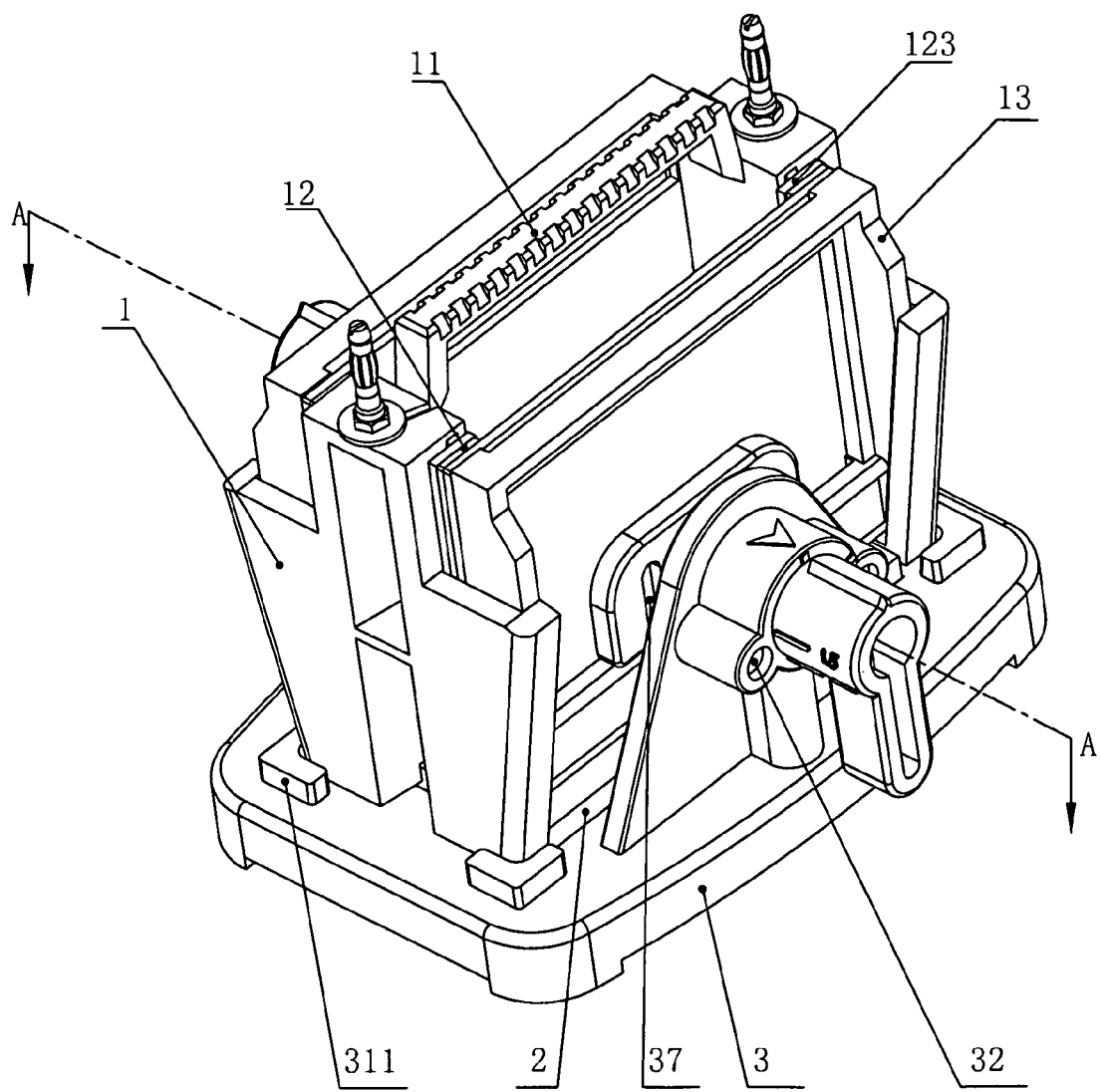
FIG. 1 is a perspective view of the whole structure according to one embodiment of the invention.
Figure 2:
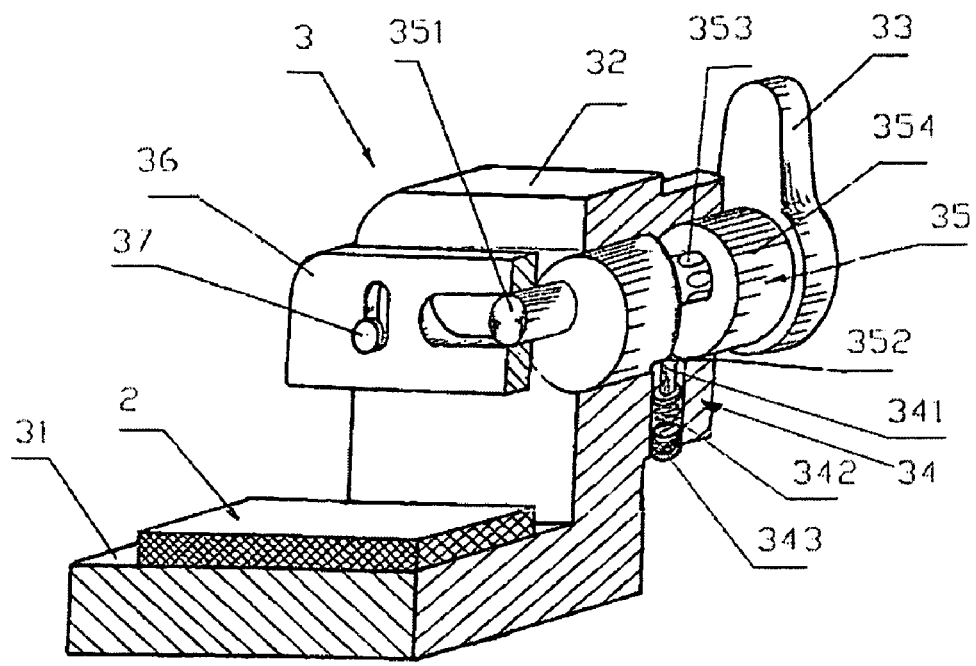
FIG. 2 is a perspective view of the internal structure according to one embodiment of the invention.
Figure 2A:
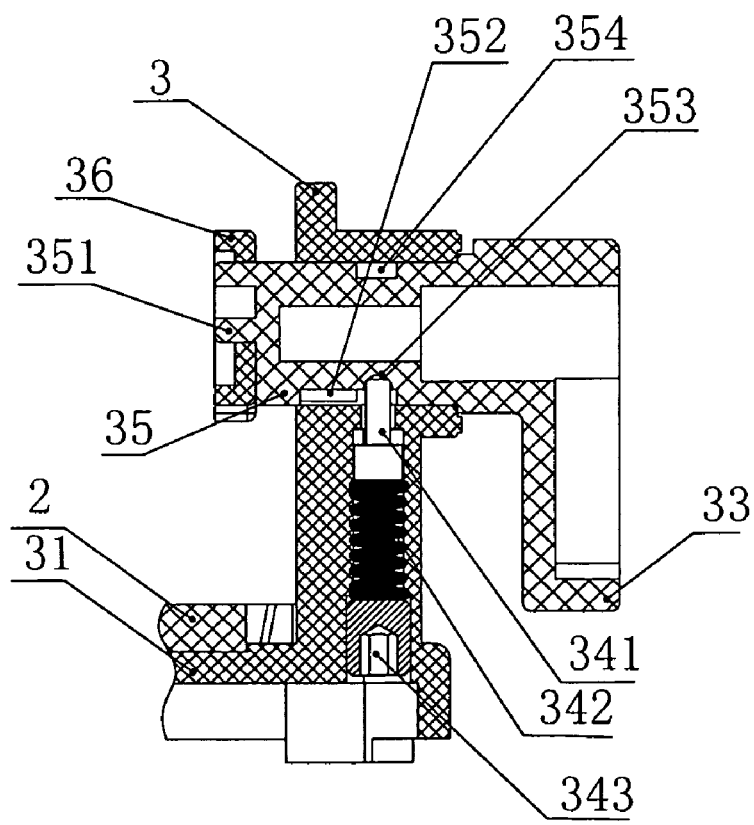
Figure 3:
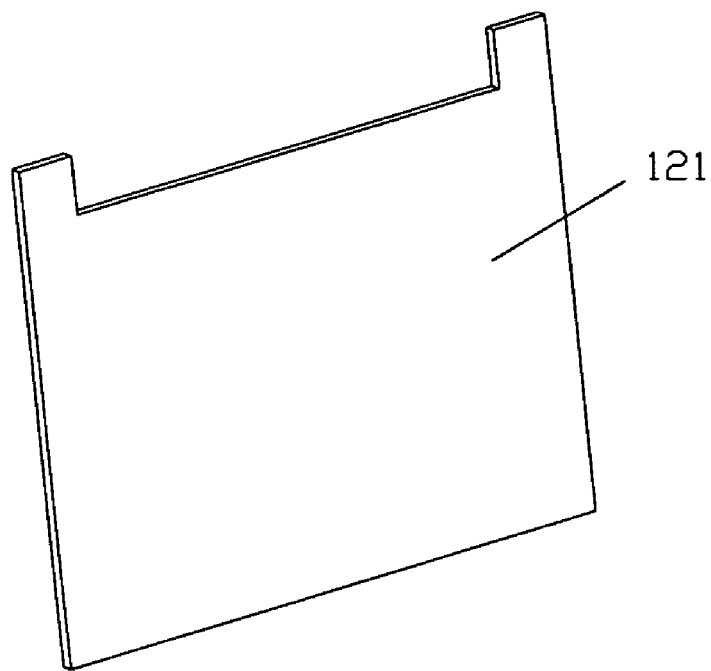
FIG. 3 is a perspective view of the notched glass according to one embodiment of the invention.
Figure 4:
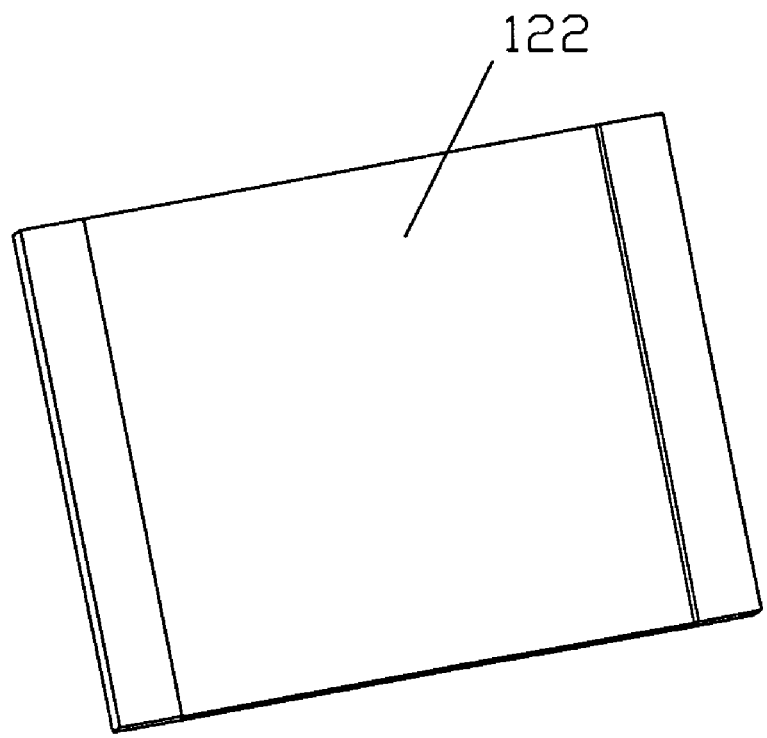
FIG. 4 is a perspective view of the glass plate with the spacer of according to one embodiment of the invention.

As the figures showing, an "In-Situ Gel Casting machine" that comprising a gel casting stand (1), a silicone cushion (2), and a locking base (3);

The gel-casting stand (1) consists of a portable casting stand (11), two slab gel casting molds (12) and two wedge frames (13). Each of slab gel casting molds (12) mainly contains a notched glass (121) and a glass plate (122) with spacer. Overlapping the notched glass (121) with the glass plate (122) tightly together forms a slab gel casting mold (123). The gel-casting stand (1) is formed by putting the same two slab gel casting molds (12) into each side of the portable casting stand (11) along its insides, and then insert the wedge frames (13) against each slab gel casting mold (12).

The locking base (3) consists of a base (31) with four locking blocks (311) and two sidewall-locking structures (32). Each of the two sidewall-locking structures (32) contains an eccenter axis body (35), a drive pin (34) and a pressing plate (36). The eccenter axis body (35) along its axis consists of eccenters (351), a U-slot stop (352), a pin roll locating hole (353), O-slot (354) and a handle (33). Each lower part of the sidewall locking structure (32) has the drive pin (34) matching with the U-slot stop (352) and the O-slot (354). Each drive pin (34) consists of a bolt (343), a spring (342) and a pin (341) that can be elastically extended and compressed in the vertical direction. On the sidewall-locking structures (32), the press plate (36) is provided that face to the inside of the locking base (3). The press plate (36) hitches on the eccenter (351) and connects with a horizontal leading pole (37) that supports the press plate (36).

The overall structure of the "In-Situ Gel Casting machine" is as follows: the silicone cushion (2) is set on the base (31) of the locking base (3), and the gel-casting stand (1) is put onto the locking base (3) within the four locking blocks (311). Then, push the handles (33) inwardly while the pins (341) of the drive pins (34) are in the U-slot stops (352) and move the press plates (36) to a proper distance to the slab gel casting molds (12). After this, turn the handles (33) clockwise and set the press plates (36) onto the lower beams of the wedge frames (13), which get the pins (341) of the drive pins (34) in the pin roll locating holes (353). Therefore, the press plates (36) will push the wedge frames that automatically compress the slab gel casting molds (12) tightly from two directions.

Before the gel is casted, the gel casting mold is to be formed by overlapping the notched glass plates (121) with the spacer glass plates (122), which will assemble the slab gel casting mold (123). Put the slab gel casting mold (123) into the gel-casting stand (1) and keep the notched glass plates against inside walls of gel-casting stand. Insert the wedge frames (13) against the slab gel casting mold (123). Press the wedge frames down so that the gel rooms can be compressed. Then set the gel casting stand (1) onto the base (31) within the area formed by the four pieces of the locking blocks (311), and make sure the bottom of the gel casting stand (1) touch the silicone cushion (2) well. At this time the pins (341) of the drive pins (34) are in the U-slot stops (352), the handles of the sidewall locking structure (32) are set downward. We call it the initial state. At this state, neither the two handles neither (33) nor the eccenter axis bodies (35) can be turned around optionally, but they can be pushed horizontally toward inside of the gel-casting stand. As the handles are pushed to their limits (33), they can be turned around in a certain angle. Then, the pins (341) of the drive pins (34) can be moved into the pin roll locating holes (353) and the sidewall locking structures (32) are in the lock state. At this time, the two handles (33) cannot be moved horizontally, but they can be turned around optionally. At the initial state, the purposes of setting the two handles (33) to be pushed in or sprung out horizontally only, not to be turned around, are to prevent the wrong operation that can cause the damage to the machine and to make sure the silicone cushion (2) is at the center of the bottom (31). After the set up, the thickness of the slab gel casting molds (12) and the height of the wedge frames (13) can be adjusted respect to the types of a gel is going to be used in a particular experiment. The pattern is that the positions of the wedge frames (13) go higher as the slab gel casting molds (12) get thicker. In addition, the wedge frames (13) are moved up and down by the movement of the press plates (36) as we turning around the handles (33). Turn around the handles (33) to a relevant position where the mark points to a certain thickness, and then the press plates (36) will press the wedge frames tightly and lock them. Now, the machine has been set up and a user can start to cast gel.

The working concept of this new machine is to use the rotation of the eccenter axis bodies (35) to move the press plates (36) up and down in order to press the wedge frames (13) that automatically compress the slab gel casting molds tightly. Because the force is directly adding on the wedge frames (13), which can ensure the slab gel casting molds (12) are in fixed positions. This development has prevented both the leakage of the gel solution and the production of the air into the slab gel casting molds (12) during the gel casting.

What is claimed is:

1. An in-situ gel casting machine comprising:
   a gel-casting stand device including a portable casting stand with a pair of wedge groove, a slab gel casting mold and a wedge frame both being inserted into the wedge groove and both being clamped together by a clamping force brought from the wedge groove;
   a base having four locking blocks to defined a area in which the gel-casting stand device is located movably;
   a sidewall locking device for pushing the wedge frame into the wedge groove further for getting a strong clamping force from the wedge groove;
   a rubber cushion being set on the base within the four locking blocks, the gel-casting stand device seating on the rubber cushion.

2. The in-situ gel casting machine of claim 1, wherein there are two gel-casting stand devices, two pairs of wedge groove, two wedge frames and two sidewall locking devices located symmetrically in the machine.

3. The in-situ gel casting machine of claim 1, wherein the slab gel casting mold is formed by overlapping a notched glass and a glass plate with a spacer together to form a gel room.

4. The in-situ gel casting machine of claim 1, wherein the sidewall locking device including an eccenter axis body having an eccenter at one end and a handle at other end, a press plate is connected with the eccenter, the eccenter pushes the press plate down when the handle is turned, in turn the press plate pushes the wedge frame into the wedge groove further.

5. The in-situ gel casting machine of claim 4, wherein further has a drive pin with a moveable bolt, the eccenter axis body has a U-slot stop and a O-slot, when the bolt blocks in the U-slot stop, the eccenter axis body can be pushed horizontally toward inside of the gel-casting stand device, when the bolt blocks in the O-slot the eccenter axis body can be only turned around optionally.

6. The in-situ gel casting machine of claim 5, wherein the drive pin includes the bolt and a spring, the spring pushes the bolt being elastically extended out or compressed in.

7. The in-situ gel casting machine of claim 1, wherein the rubber cushion is a silicone cushion.

8. The in-situ gel casting machine of claim 1, wherein the two wedge grooves are located two sides of the portable casting stand, the wedge frame has two wedges corresponding to the two wedge grooves located on two side of the wedge frame.

9. The in-situ gel casting machine of claim 5, wherein the eccenter axis body has several pin roll locating holes, the bolt can be inserted into the pin roll locating hole for controlling the locking state of the gel-casting stand device.

* * * * *